United States Patent
Weber et al.

Patent Number: 5,543,280
Date of Patent: Aug. 6, 1996

[54] COLOUR PHOTOGRAPHIC RECORDING MATERIAL

[75] Inventors: Beate Weber, Leichlingen; Jörg Hagemann, Cologne; Günter Helling, Odenthal; Markus Geiger, Langenfeld, all of Germany

[73] Assignee: AGFA-Gevaert AG, Germany

[21] Appl. No.: 557,734

[22] Filed: Nov. 13, 1995

[30] Foreign Application Priority Data

Nov. 24, 1994 [DE] Germany .......................... 44 41 847.7

[51] Int. Cl.$^6$ ................................. G03C 7/392
[52] U.S. Cl. .......................... 430/503; 430/551; 430/556; 430/557
[58] Field of Search ................... 430/503, 551, 430/556, 557

[56] References Cited

U.S. PATENT DOCUMENTS

| | | | |
|---|---|---|---|
| 3,700,455 | 10/1972 | Ishikawa et al. | 430/551 |
| 5,399,473 | 3/1995 | Shono et al. | 430/556 |
| 5,418,121 | 5/1995 | Yoshioka et al. | 430/551 |

FOREIGN PATENT DOCUMENTS

| | | | |
|---|---|---|---|
| 0247240 | 12/1995 | Japan | 430/551 |

Primary Examiner—Lee C. Wright
Attorney, Agent, or Firm—Connolly & Hutz

[57] ABSTRACT

A color photographic material which contains in at least one blue sensitive layer containing a yellow coupler a compound of the formula (I)

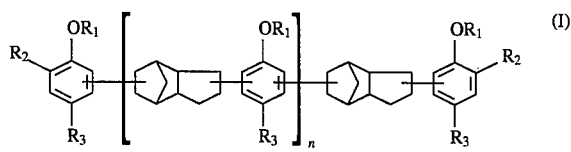

in which $R_1$ means $-(X)_m-R_4$, m means 0 or 1,

X means $-CO-$, $-CO-NR_5-$ or $-CO-O-$, $R_4$ means H, alkyl, aryl or alkenyl, $R_2$ means H or alkyl, $R_3$ means H or alkyl, $R_5$ means H, alkyl, cycloalkyl or aryl, n means 1 to 20, providing that m is 1 in at least 10% of the $R_1$ groups, is distinguished by improved color stability.

9 Claims, No Drawings

COLOUR PHOTOGRAPHIC RECORDING MATERIAL

This invention relates to a colour photographic recording material with improved colour stability.

Colour photographic materials customarily contain at least one yellow coupler, at least one magenta coupler and at least one cyan coupler from which the corresponding dyes are produced by exposure and development. These dyes, particularly those dyes constantly exposed to light, should have elevated colour stability, wherein particular value is attached to all three colours having colour stability which is as far as possible equally good so that in the event of slight fading, no colour distortion occurs.

In particular, yellow dyes produced from couplers with an open-chain ketomethylene grouping must be stabilised both against light and against dark fading.

It has already been proposed in U.S. Pat. No. 3,700,455 to achieve this object with bisphenol compounds as stabilisers. The effect achieved with them is, however, still inadequate.

It has now surprisingly been found that very specific polycyclic phenols may achieve this object much more effectively.

The present invention thus provides a colour photographic material which contains on a support at least one blue-sensitive silver halide emulsion layer containing at least one yellow coupler, at least one green-sensitive silver halide emulsion layer containing at least one magenta coupler, at least one red-sensitive silver halide emulsion layer containing at least one cyan coupler, together with customary non-photosensitive layers, characterised in that at least one blue-sensitive layer containing a yellow coupler contains a compound of the formula (I)

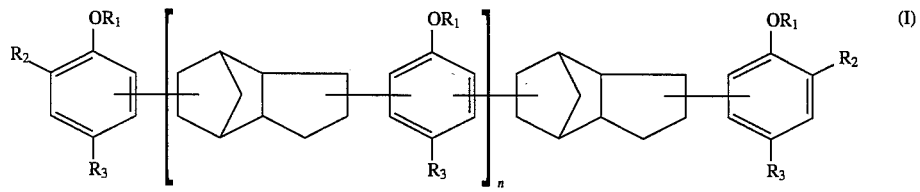

in which $R_1$ means $-(X)_m-R_4$, m means 0 or 1,

X means $-CO-$, $-CO-NR_5-$ or $-CO-O-$, $R_4$ means H, alkyl, aryl or alkenyl, $R_2$ means H or alkyl, $R_3$ means H or alkyl, $R_5$ means H, alkyl, cycloalkyl or aryl, n means 1 to 20, preferably 2 to 8, providing that m is 1 in at least 10% of the $R_1$ groups.

The alkyl groups $R_2$, $R_3$ and $R_4$ and the alkenyl groups $R_4$ may be unbranched, branched or cyclic and unsubstituted or substituted. They preferably have 1 to 12 C atoms and are no further substituted. The aryl group $R_4$ may be unsubstituted or substituted. The residues $R_2$, $R_3$ and $R_4$ may be identical to or different from each other.

Preferably, all residues $R_3$ are alkyl and all residues $R_2$ branched alkyl, in particular tert.-butyl. X is preferably $-CO-$ or $-COO-$. $R_4$ is preferably alkyl or alkenyl.

In a preferred embodiment at least 20%, preferably 30% to 80% of the groups $-(X)_m-R_4$ are hydrogen atoms.

If m is 1, $R_4$ is preferably not hydrogen. Suitable compounds of the formula (I) are:

| | | |
|---|---|---|
| I-1: | $R_1 = H$; $-COC(CH_3)=CH_2$ in a 1:1 molar ratio, | $\bar{M}_w = 1500$ |
| I-2: | $R_1 = H$; $-COCH=CH_2$ 3:1 | $\bar{M}_w = 1450$ |
| I-3: | $R_1 = H$; $-COOC_2H_5$ 1:1 | $\bar{M}_w = 1500$ |
| I-4: | $R_1 = H$; $-CONHC_{12}H_{25}$ 1:1 | $\bar{M}_w = 1650$ |
| I-5: | $R_1 = H$; $-COCH_3$ 1:1 | $\bar{M}_w = 1430$ |
| I-6: | $R_1 = H$; $-C_2H_5$ 1:1 | $\bar{M}_w = 1500$ |
| I-7: | $R_1 = H$; $-COCH=CH_2$ 1:1 | $\bar{M}_w = 1500$ |

| | | |
|---|---|---|
| I-8: | $R_1 = H$; $-COCH=CH_2$ 1:1 $R_2, R_3 = CH_3$ | $M_w = 1350$ |
| I-9: | $R_1 = H$; $-CO-CH=CH_2$ 1:1 $R_2 = i-C_3H_7, R_3 = t-C_4H_9$ | $M_w = 1200$ |
| I-10: | $R_1 = H$; $-CO-CH=CH_2$ 1:1 $R_2 = $ cyclohexyl, $R_3 = CH_3$ | $\bar{M}_w = 1500$ |
| I-11: | $R_1 = H$; $-COCH_3$ 3:1 $R_2 = $ 1-methylcyclohexyl, $R_3 = CH_3$ | $\bar{M}_w = 1400$ |
| I-12: | $R_1 = H$; $-COOC_2H_5$ 3:1 $R_2 = i-C_3H_7, R_3 = t-C_4H_9$ | $\bar{M}_w = 1200$ |

The compounds of the formula I are added to at least one blue sensitive silver halide emulsion layer containing at least one yellow coupler in particular in a quantity of 0.1 to 2 mol/mol of coupler. The yellow couplers are preferably 2-equivalent pivaloyl yellow couplers, the leaving group of which is attached to the coupling position of the coupler either via oxygen or via nitrogen. The yellow couplers are preferably used in a quantity of 0.5 to 1.5 mmol/m² of photographic material.

Suitable yellow couplers are:

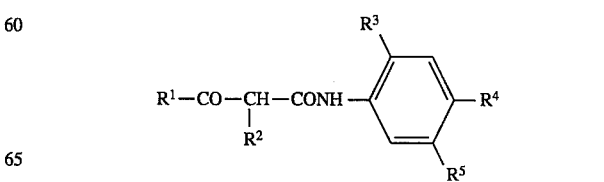

Y-1:
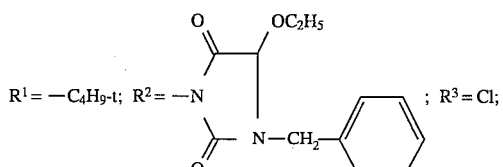
Y-2:
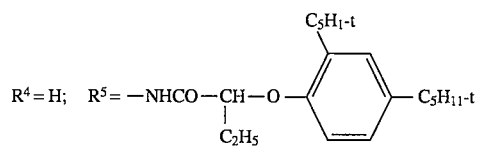
Y-3:
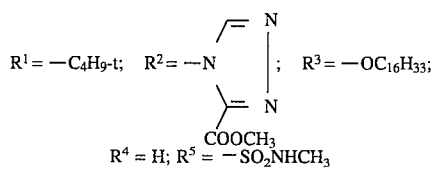
Y-4:
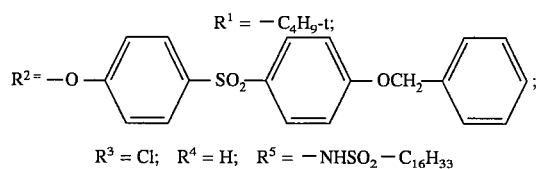
Y-5:
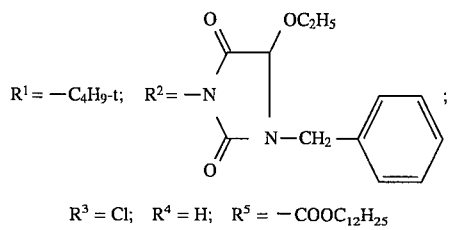
Y-6:
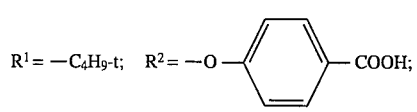
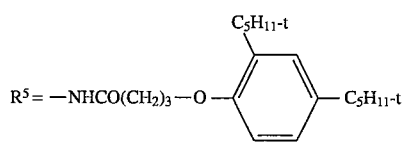
Y-7:
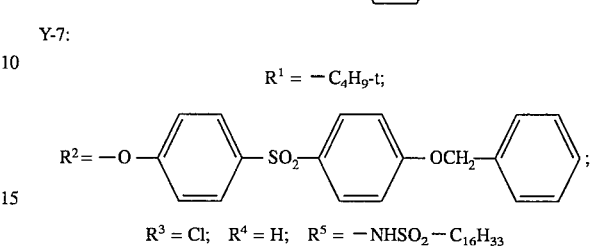
Y-8:
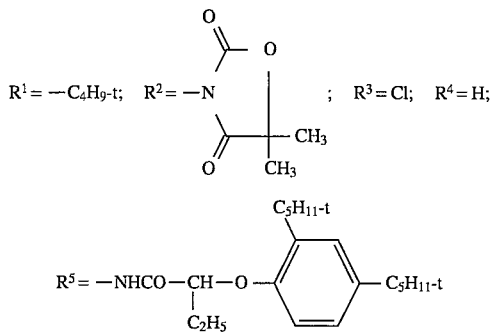
Y-9:
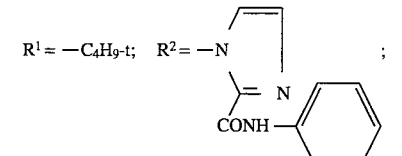
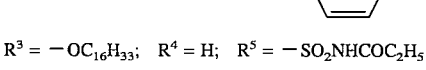
Y-10:
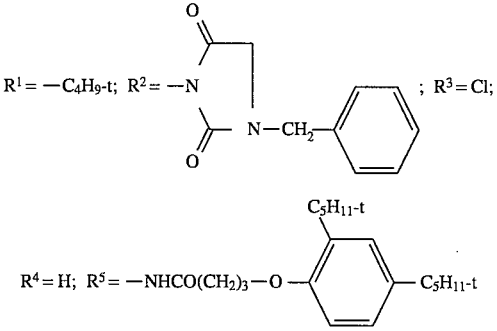
Y-11:
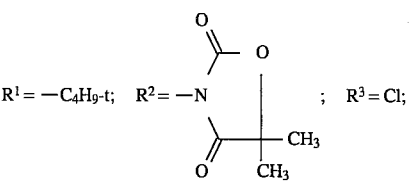

-continued
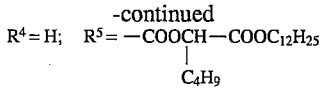
Y-12:
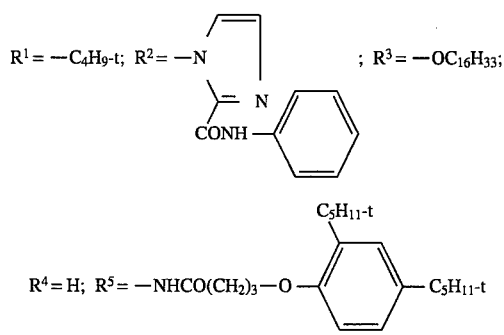
Y-13:
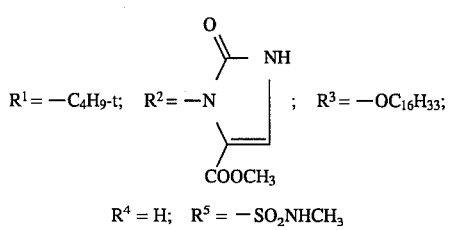
Y-14:
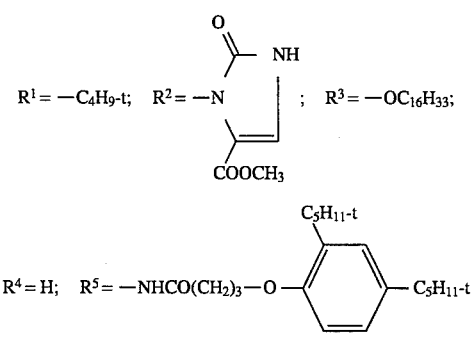
Y-15:
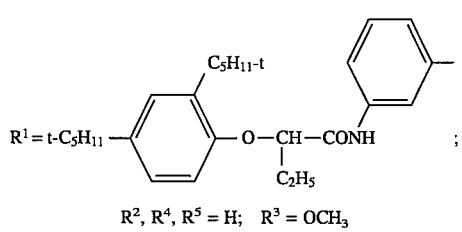
Y-16:
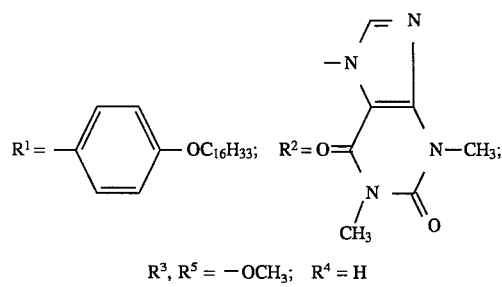
-continued
Y-17:
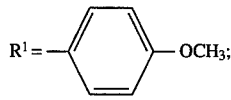
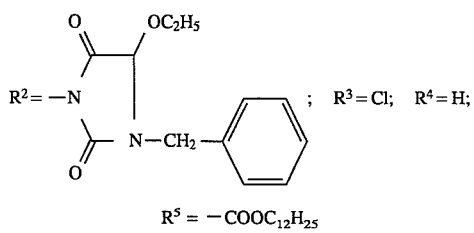
Y-18:
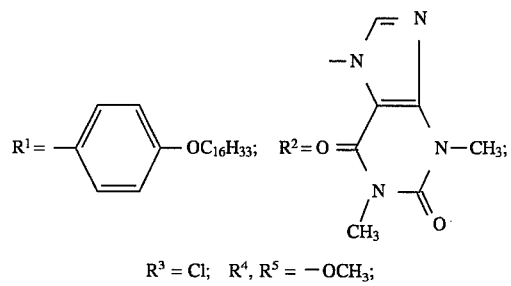
Y-19:
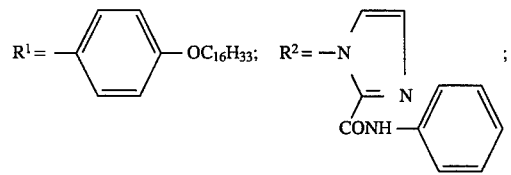
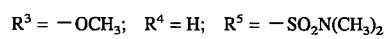
Y-20:
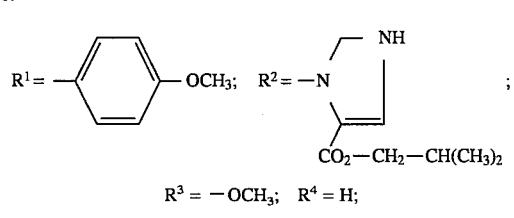
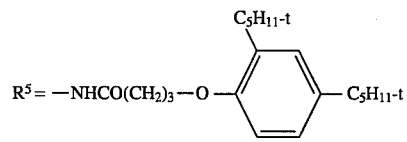
Y-21:
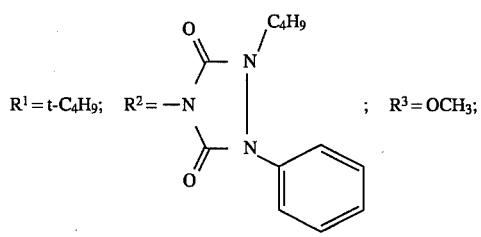

Y-22:
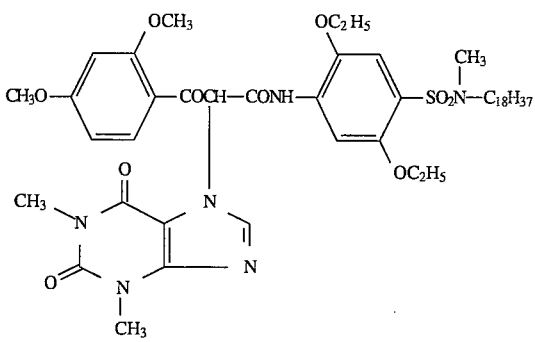

Y-23:
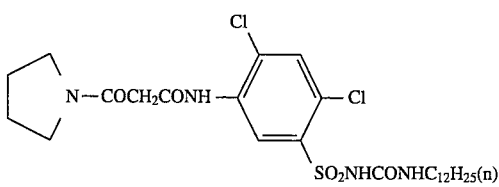

Y-24:
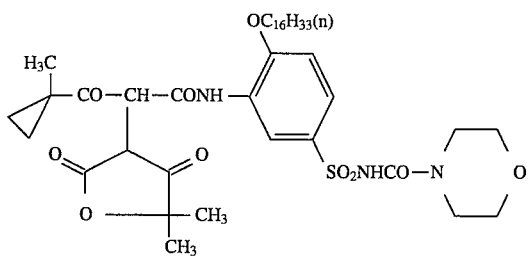

Y-25:
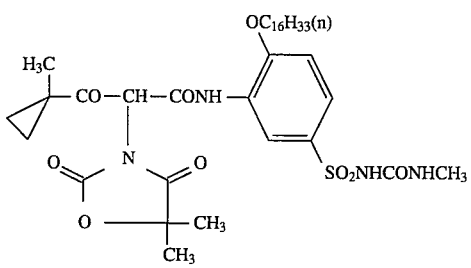

Y-26:
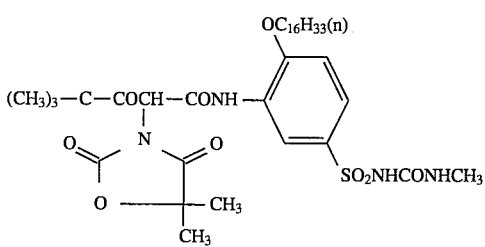

The support may be reflective or transparent.

Silver halides which may be considered for the silver halide emulsion layers are AgBr, AgBrCl, AgBrClI and AgCl.

The silver halides of all the photosensitive layers, preferably contain at least 80 mol. % chloride, in particular 95 to 100 mol. % chloride, 0 to 5 mol. % bromide and 0 to 1 mol. % iodide. The silver halide emulsions may be directly positive-working or preferably negative-working emulsions.

The silver halide crystals may be predominantly compact, for example regularly cubic or octahedral, or they may have transitional shapes. Preferably, however, twinned, for example lamellar, crystals may also be present, the average ratio of diameter to thickness of which is preferably at least 5:1, wherein the diameter of a grain is defined as the diameter of a circle the contents of which correspond to the projected surface area of the grain. The layers may, however, also have tabular silver halide crystals in which the ratio of diameter to thickness is substantially greater than 5:1, for example 12:1 to 30:1.

The silver halide grains may also have a multi-layered grain structure, in the simplest case with one internal zone and one external zone of the grain (core/shell), wherein the halide composition and/or other modifications, such as for example doping, of the individual grain zones are different. The average grain size of the emulsions is preferably between 0.2 μm and 2.0 μm, the grain size distribution may be both homodisperse and heterodisperse. The emulsions may, in addition to the silver halide, also contain organic silver salts, for example silver benzotriazolate or silver behenate.

Two or more types of silver halide emulsions which are produced separately may be used as a mixture.

The photographic emulsions may be produced by various methods (for example P. Glafkides, Chimie et Physique Photographique, Paul Montel, Paris (1967), G. F. Duffin, Photographic Emulsion Chemistry, The Focal Press, London (1966), V. L. Zelikman et al., Making and Coating Photographic Emulsion, The Focal Press, London (1966)) from soluble silver salts and soluble halides.

Gelatine is preferably used as the binder for the silver halides. Gelatine may, however, be entirely or partially replaced with other synthetic, semi-synthetic or also naturally occurring polymers.

The binders should have a sufficient quantity of functional groups available so that satisfactorily resistant layers may be produced by reaction with suitable hardeners. Such functional groups are in particular amino groups, but also carboxyl groups, hydroxyl groups and active methylene groups.

The photographic emulsions may contain compounds to prevent fogging or to stabilise the photographic function during production, storage or photographic processing.

Particularly suitable are azaindenes, preferably tetra- and pentaazaindenes, particularly those substituted with hydroxyl or amino groups. Such compounds have been described, for example, by Birr, Z. Wiss. Phot., 47, (1952), pages 2–58. Furthermore, salts of metals such as mercury or cadmium, aromatic sulphonic or sulphinic acids such as benzenesulphinic acid, or heterocyclics containing nitrogen such as nitrobenzimidazole, nitroindazole, (substituted) benzotriazoles or benzothiazolium salts may also be used as anti-fogging agents. Particularly suitable are heterocyclics containing mercapto groups, for example mercaptobenzothiazoles, mercaptobenzimidazoles, mercaptotetrazoles, mercaptothiadiazoles, mercaptopyrimidines, wherein these mercaptoazoles may also contain a water solubilising group, for example a carboxyl group or sulpho group. Further suitable compounds are published in Research Disclosure 17643 (December 1978), section VI.

The stabilisers may be added to the silver halide emulsions before, during or after ripening of the emulsions. Naturally, the compounds may also be added to other photographic layers which are associated with a silver halide layer.

Mixtures of two or more of the stated compounds may also be used.

The silver halide emulsions are customarily chemically ripened, for example by the action of gold compounds or compounds of divalent sulphur.

The photographic emulsion layers or other hydrophilic colloidal layers of the photosensitive material produced according to the invention may contain surface-active agents for various purposes, such as coating auxiliaries, to prevent formation of electric charges, to improve sliding properties, to emulsify the dispersion, to prevent adhesion and to improve photographic characteristics (for example acceleration of development, high contrast, sensitisation etc.).

Suitable sensitising dyes are cyanine dyes, in particular those of the following classes:

1. Red sensitisers Dicarbocyanines with naphthothiazole or benzothiazole as basic terminal groups, which may be substituted in the 5- and/or 6-position by halogen, methyl, methoxy, together with 9,11-alkylene-bridged, in particular 9,11-neopentylenethiadicarbocyanines having alkyl or sulphoalkyl substituents on the nitrogen.
2. Green sensitisers 9-Ethyloxacarbocyanines which are substituted in the 5-position by chlorine or phenyl and bear alkyl or sulphoalkyl residues, preferably sulphoalkyl substituents, on the nitrogen of the benzoxazole groups.
3. Blue sensitisers Methinecyanines having benzoxazole, benzothiazole, benzoselenazole, naphthoxazole, naphthothiazole as basic terminal groups which may be substituted in the 5- and/or 6-position by halogen, methyl, methoxy and bear at least one, preferably two, sulphoalkyl substituents on the nitrogen. Apomerocyanines having a rhodanine group are also suitable.

The differently sensitised emulsion layers are associated with non-diffusing monomeric or polymeric colour couplers which may be located in the same layer or in an adjacent layer.

Colour couplers to produce the cyan partial colour image are generally couplers of the phenol or α-naphthol type or of the pyrazolotriazole type.

Colour couplers to produce the magenta partial colour image are generally couplers of the pyrazoloazole, 5-pyrazolone, indazolone or iminodicyanoethylene type.

Colour couplers to produce the yellow partial colour image are generally couplers with an open-chain ketomethylene grouping, in particular couplers of the α-acylacetamide and carbamoylacetamide type; suitable examples of these are α-benzoylacetanilide couplers and α-pivaloylacetanilide couplers. As already mentioned, the latter are preferred.

The colour couplers may be 4-equivalent couplers, but they may also be 2-equivalent couplers. The latter are differentiated from 4-equivalent couplers by containing a substituent at the coupling site which is eliminated on coupling.

The couplers customarily contain a ballast residue in order to make diffusion within the material, i.e. both within a layer or from layer to layer, impossible. High molecular weight couplers may also be used instead of couplers with a ballast residue.

Suitable colour couplers and literature references in which these are described may be found in Research Disclosure 307 109 (1989), section VII and WO 94/07 534.

High molecular weight colour couplers are, for example, described in DE-C-1 297 417, DE-A-24 07 569, DE-A-31 48 125, DE-A-32 17 200, DE-A-33 20 079, DE-A-33 24 932, DE-A-33 31 743, DE-A-33 40 376, EP-A-27 284, U.S. Pat. No. 4,080,211. The high molecular weight colour couplers are generally produced by polymerisation of ethylenically unsaturated monomeric colour couplers. They may, however, also be obtained by polyaddition or polycondensation.

The incorporation of couplers or other compounds into the silver halide emulsion layers may proceed by initially producing a solution, dispersion or emulsion of the compound concerned and then adding it to the pouring solution for the layer concerned. Selection of the appropriate solvent or dispersant depends on the particular solubility of the compound.

Methods for the introduction of compounds which are substantially insoluble in water by a grinding process are described, for example, in DE-A-26 09 741 and DE-A-26 09 742.

Hydrophobic compounds may also be introduced into the pouring solution by using high-boiling solvents, so-called oil formers. Corresponding methods are described, for example, in U.S. Pat. Nos. 2,322,027, 2,801,170, 2,801,171 and EP-A-0 043 037.

Oligomers or polymers, so-called polymeric oil formers, may be used instead of high-boiling solvents.

The compounds may also be introduced into the pouring solution in the form of filled latices. Reference is, for example, made to DE-A-25 41 230, DE-A-25 41 274, DE-A-28 35 856, EP-A-0 014 921, EP-A-0 069 671, EP-A-0 130 115, U.S. Pat. No. 4,291,113.

The non-diffusible inclusion of anionic water-soluble compounds (for example of dyes) may also proceed with the assistance of cationic polymers, so-called mordanting polymers.

Suitable oil formers are, for example, phthalic acid alkyl esters, phosphonic acid esters, diphenic acid esters and amides, phosphoric acid esters, citric acid esters, benzoic acid esters, amides, fatty acid esters and amides, trimesic acid esters, alcohols phenols aniline derivatives, hydrocarbons, sulphones, sulphonamides and sulphoxides.

Examples of suitable oil formers are dibutyl phthalate, dicyclohexyl phthalate, di-2-ethylhexyl phthalate, decyl phthalate, triphenyl phosphate, tricresyl phosphate, 2-ethylhexyldiphenyl phosphate, tricyclohexyl phosphate, tri-2-ethylhexyl phosphate, tridecyl phosphate, tributoxyethyl phosphate, trichloropropyl phosphate, di-2-ethylhexylphenyl phosphate, 2-ethylhexyl benzoate, dodecyl benzoate, 2-ethylhexyl-p-hydroxybenzoate, diethyldodecanamide, N-tetradecylpyrrolidone, isostearyl alcohol, 2,4-di-tert.-amylphenol, dioctyl acetate, glycerol tributyrate, isostearyl lactate, trioctyl citrate, N,N-dibutyl-2-butoxy-5-tert.-octyl aniline, paraffin, dodecyl benzene and diisopropylnaphthalene.

The photographic material may also contain UV light absorbing compounds, optical whiteners, spacers, filter dyes, formalin scavengers, light stabilisers, anti-oxidants, $D_{min}$ dyes, additives to improve stabilisation of dyes, couplers and whites and to reduce colour fogging, plasticisers (latices), biocides and others. Interlayers may moreover contain so-called white couplers and other compounds which react with the developer oxidation product (scavengers).

The layers of the photographic material may be hardened with customary hardeners. Suitable hardeners are, for example, formaldehyde, glutaraldehyde and similar aldehyde compounds, diacetyl, cyclopentadione and similar ketone compounds, bis-(2-chloroethylurea), 2-hydroxy-4,6-dichloro-1,3,5-triazine and other compounds containing reactive halogen (U.S. Pat. Nos. 3,288,775, 2,732,303, GB-A-974,723 and GB-A-1,167,207), divinylsulphone compounds, 5-acetyl-1,3-diacryloylhexahydro-1,3,5-triazine and other compounds containing a reactive olefin bond (U.S. Pat. Nos. 3,635,718, 3,232,763 and GB-A-994,869); N-hydroxymethylphthalimide and other N-methylol compounds (U.S. Pat. Nos. 2,732,316 and 2,586,168); isocyanates (U.S. Pat. No. 3,103,437); aziridine compounds (U.S. Pat. Nos. 3,017,280 and 2,983,611); acid derivatives (U.S. Pat. Nos. 2,725,294 and 2,725,295); compounds of the carbodiimide type (U.S. Pat. No. 3,100,704); carbamoylpyridinium salts (DE-A-22 25 230 and DE-A-24 39 551); carbamoyloxypyridinium compounds (DE-A-24 08 814); compounds with a phosphorus-halogen bond (JP-A-113 929/83); N-carbonyloximide compounds (JP-A-43353/81); N-sulphonyloximido compounds (U.S. Pat. No. 4,111,926), dihydroquinoline compounds (U.S. Pat. No. 4,013,468), 2-sulphonyloxypyridinium salts (JP-A-110 762/81), formamidinium salts (EP-A-0 162 308), compounds with two or more N-acyloximino groups (U.S. Pat. No. 4,052,373), epoxy compounds (U.S. Pat. No. 3,091,537), compounds of the isoxazole type (U.S. Pat. Nos. 3,321,313 and 3,543,292); halogen carboxyaldehydes, such as mucochloric acid; dioxane derivatives, such as dihydroxydioxane and dichlorodioxane; and inorganic hardeners such as chrome alum and zirconium sulphate.

Hardening may be effected in a known manner by adding the hardener to the pouring solution for the layer to be hardened, or by overcoating the layer to be hardened with a layer containing a diffusible hardener.

There are included in the classes listed slow acting and fast acting hardeners as well as so-called instant hardeners, which are particularly advantageous. Instant hardeners are taken to be compounds which harden suitable binders in such a way that immediately after pouring, at the latest after 24 hours, preferably at the latest after 8 hours, hardening is concluded to such an extent that there is no further alteration in the sensitometry and swelling of the layered structure determined by the crosslinking reaction. Swelling is taken to be the difference between the wet layer thickness and the dry layer thickness during aqueous processing of the film (Photogr. Sci. Eng. 8 (1964), 275; Photogr. Sci. Eng. (1972), 449).

These hardeners which react very rapidly with gelatine are, for example, carbamoylpyridinium salts, which are capable of reacting with the free carboxyl groups of the gelatine, so that the latter react with free amino groups of the gelatine to form peptide bonds crosslinking the gelatine.

There exist diffusible hardeners which have an equal hardening action on all the layers within a layer structure. However, there also exist other hardeners, which may be low molecular weight or high molecular weight compounds, which are non-diffusible and limited in their action to the layer in which they are located. These may be used to bring about particularly dense crosslinking of individual layers, for example the protective layer. This is important if the silver halide layer is hardened only slightly in order to increase silver covering power and mechanical properties must be improved with the protective layer (EP-A 0 114 699).

The photographic materials according to the invention are customarily processed by developing, bleaching, fixing and rinsing or stabilising without subsequent rinsing, wherein bleaching and fixing may be combined into a single processing stage. Colour developer compounds which may be used are all developer compounds having the ability to react, in the form of their oxidation product, with colour couplers to form azomethine or indophenol dyes. Suitable colour developer compounds are aromatic compounds containing at least one primary amino group of the p-phenylenediamine type, for example N,N-dialkyl-p-pheneylenediamines such as N,N-diethyl-p-phenylenediamine, 1-(N-ethyl-N-methanesulphonamidoethyl)-3-methyl-p-phenylenediamine, N-ethyl-N-3-hydroxypropyl-3-methyl-p-phenylenediamine and 1-(N-ethyl-N-methoxyethyl)-3-methyl-p-phenylenediamine. Further usable colour developers are, for example, described in J. Amer. Chem. Soc. 73, 3106 (1951) and G. Haist Modern Photographic Processing, 1979, John Wiley & Sons, New York, pages 545 et seq.

An acid stop bath or rinsing may follow after colour development.

Customarily, the material is bleached and fixed after colour development. Bleaches which may be used are, for example, Fe(III) salts and Fe(III) complex salts such as ferricyanides, dichromates, water soluble cobalt complexes. Iron(III) complexes of aminopolycarboxylic acids are particularly preferred, in particular for example complexes of ethylenediaminetetraacetic acid, propylenediaminetetraacetic acid, diethylenetriaminepentaacetic acid, nitrilotriacetic acid, iminodiacetic acid, N-hydroxyethylethylenediaminetriacetic acid, alkyliminodicarboxylic acids and of corresponding phosphonic acids. Persulphates and peroxides, for example hydrogen peroxide, are also suitable as bleaches.

Rinsing usually follows the bleaching-fixing bath or fixing bath, which is performed as countercurrent rinsing or comprises several tanks with their own water supply.

Favourable results may be obtained by using a subsequent finishing bath which contains no or only a little formaldehyde.

Rinsing may, however, be completely replaced with a stabilising bath, which is customarily operated countercurrently. If formaldehyde is added, this stabilising bath also performs the function of a finishing bath.

EXAMPLE 1

The following two layers were applied onto a paper coated on both sides with polyethylene. In each case, the quantities relate to one m².

1st layer Blue sensitive silver halide emulsion layer prepared from 0.6 g of AgNO$_3$ (99.5 mol. % chloride, 0.5 mol. % bromide, average grain diameter 0.78 μm) 2 g gelatine 0.8 g yellow coupler Y-21 0.6 g TCP 0.2 g stabiliser according to table 1

2nd layer 2 g gelatine 0.4 g hardener of the formula

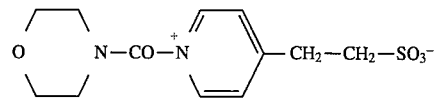

The samples were then exposed behind a graduated grey wedge and processed in the customary manner with the processing baths listed below.

a) Colour developer—45 s—35° C.

| | |
|---|---|
| Triethanolamine | 9.0 g/l |
| N,N-diethylhydroxylamine | 4.0 g/l |
| Diethylene glycol | 0.05 g/l |
| 3-methyl-4-amino-N-ethyl-N-methane-sulphonamidoethyl-aniline sulphate | 5.0 g/l |
| Potassium sulphite | 0.2 g/l |
| Triethylene glycol | 0.05 g/l |
| Potassium carbonate | 22 g/l |
| Potassium hydroxide | 0.4 g/l |

-continued

| Ethylenediaminetetraacetic acid, disodium salt | 2.2 g/l |
| Potassium chloride | 2.5 g/l |
| 1,2-Dihydroxybenzene-3,4,6-trisulphonic acid, trisodium salt | 0.3 g/l |
| make up to 1000 ml with water; pH 10.0 | | b) Bleaching/fixing bath—45 s—35° C.

| Ammonium thiosulphate | 75 g/l |
| Sodium hydrogen sulphite | 13.5 g/l |
| Ammonium acetate | 2.0 g/l |
| Ethylenediaminetetraacetic acid (iron-ammonium salt) | 57.0 g/l |
| 25% ammonia | 9.5 g/l |
| Acetic acid | 9.0 g/l |
| make up to 1000 ml with water; pH 5.5 | | c) Rinsing—2 min—35° C.
d) Drying

The processed samples are then covered with a UV protective film and irradiated in a xenon tester to determine light fastness ($10 \cdot 10^6$ 1×h).

The UV protective film was produced as follows: a layer prepared from 1.5 g of gelatine, 0.65 g of UV absorber of the following formula

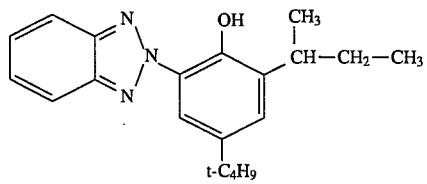

0.07 g of dioctylhydroquinone and 0.36 g of tricresyl phosphate were applied to a transparent cellulose triacetate film provided with a coating of a coupling agent.

TABLE 1

| Sample | | Stabiliser | Percentage decrease in density at density | | |
| --- | --- | --- | --- | --- | --- |
| | | | 0.6 | 1.0 | 1.4 |
| 1 | Comparison | — | 21 | 19 | 34 |
| 2 | Comparison | V-1 | 24 | 16 | 17 |
| 3 | Invention | I-2 | 14 | 10 | 11 |
| 4 | Invention | I-7 | 11 | 9 | 12 |
| 5 | Invention | I-5 | 15 | 12 | 13 |
| 6 | Invention | I-12 | 10 | 9 | 11 |

As is shown by table 1, improved light stability of the yellow dyes is achieved with the compounds according to the invention.

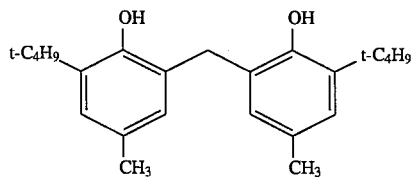

We claim:

1. A color photographic material which comprises on a support at least one blue sensitive silver halide emulsion layer containing at least one yellow coupler, at least one green sensitive silver halide emulsion layer containing at least one magenta coupler, at least one red sensitive silver halide emulsion layer containing at least one cyan coupler, wherein at least one blue sensitive layer containing a yellow coupler contains a compound of the formula (I)

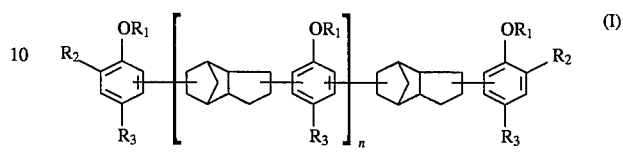

in which $R_1$ means $—(X)_m—R_4$, m means 0 or 1,

X means —CO—, —CO—NR$_5$— or —CO—O—, $R_4$ means H, alkyl, aryl or alkenyl, $R_2$ means H or alkyl, $R_3$ means H or alkyl, $R_5$ means H, alkyl, cycloalkyl or aryl, n means 1 to 20, providing that m is 1 in at least 10% of the $R_1$ groups.

2. The color photographic material according to claim 1, wherein the compound of the formula I is used in a quantity of 0.1 to 2 mol/mol of coupler in at least one blue sensitive silver halide emulsion layer containing at least one yellow coupler.

3. The color photographic silver halide material according to claim 1, wherein the yellow coupler is a 2-equivalent coupler, the leaving group of which is attached to the coupling position of the coupler either via oxygen or via nitrogen.

4. The color photographic silver halide material according to claim 1, wherein at least 80 mol. % of the silver halide emulsions are AgCl emulsions.

5. The color photographic silver halide material according to claim 1, wherein at least 20% of the groups $—(X)_m—R_4$ are hydrogen atoms.

6. The color photographic silver halide material according to claim 1, wherein 30 to 80% of the groups $—(X)_m—R_4$ are hydrogen atoms.

7. The color photographic material as claimed in claim 1 wherein n is from 2 to 8, all residues $R_3$ are alkyl and all residues $R_2$ are t-butyl, X is —CO— or —COO— and $R_4$ is alkyl or alkenyl.

8. The color photographic silver halide material as claimed in claim 7, wherein m is 1 and $R_4$ is not hydrogen atoms.

9. The color photographic silver halide material as claimed in claim 1, wherein m is 1 and $R_4$ is not hydrogen atoms.

* * * * *